United States Patent
Thalhammer et al.

(10) Patent No.: US 9,354,329 B2
(45) Date of Patent: May 31, 2016

(54) X-RAY CAMERA FOR THE HIGH-RESOLUTION DETECTION OF X-RAYS

(75) Inventors: Stefan Thalhammer, Munich (DE); Markus Hofstetter, Neubiberg (DE); John Howgate, Munich (DE); Martin Stutzmann, Erding (DE)

(73) Assignee: Helmholtz Zentrum Muenchen Deutsches Forschungszentrum fuer Gesundheit und Umwelt (Gmbh), Neuherberg (DE)

( * ) Notice: Subject to any disclaimer, the term of this patent is extended or adjusted under 35 U.S.C. 154(b) by 224 days.

(21) Appl. No.: 14/003,170

(22) PCT Filed: Mar. 2, 2012

(86) PCT No.: PCT/EP2012/000946
§ 371 (c)(1),
(2), (4) Date: Dec. 12, 2013

(87) PCT Pub. No.: WO2012/119741
PCT Pub. Date: Sep. 13, 2012

(65) Prior Publication Data
US 2014/0112432 A1    Apr. 24, 2014

(30) Foreign Application Priority Data
Mar. 4, 2011   (DE) .......................... 10 2011 013 058

(51) Int. Cl.
*G01T 1/24* (2006.01)
*H04N 5/32* (2006.01)
(Continued)

(52) U.S. Cl.
CPC . *G01T 1/24* (2013.01); *G01T 1/243* (2013.01); *H01L 27/1464* (2013.01); *H01L 27/14658* (2013.01); *H04N 5/32* (2013.01); *A61B 6/032* (2013.01); *H01L 27/14603* (2013.01)

(58) Field of Classification Search
CPC ........ A61B 6/032; A61B 6/4233; G01T 1/24; G01T 1/243; H01L 27/146; H01L 27/14601; H01L 27/14603; H01L 27/14658; H01L 27/1464
See application file for complete search history.

(56) References Cited

U.S. PATENT DOCUMENTS 3,265,899 A   8/1966  Bergstrom et al.
5,512,756 A   4/1996  Bayer et al.
(Continued)

FOREIGN PATENT DOCUMENTS

DE        4344252 A1    6/1995
DE   102008004748 A1    7/2008
(Continued)

OTHER PUBLICATIONS

Duboz et al., "GaN for x-ray detection", Applied Physics Letters, vol. 92, pp. 263501-1-3 (2008).
(Continued)

*Primary Examiner* — Thomas R Artman
(74) *Attorney, Agent, or Firm* — Caesar Rivise, PC

(57) ABSTRACT

The invention relates to an X-ray camera (100) for the high-resolution detection of X-rays (1), comprising a plurality of radiation detectors (10), each of which has a carrier substrate (11), a detector layer (12), and contact electrodes (13). The detector layer (12) contains GaN, lies on the carrier substrate (11), and has a thickness of less than 50 μm. The contact electrodes (13) form ohmic contacts with the detector layer (12). The X-ray camera also comprises a retaining device (20) on which the radiation detectors (10) are arranged along a specified reference line or reference surface (21). The invention also relates to a method for capturing an image of an object (2, 3) being examined using X-rays (1), said X-ray camera (100) being used in the method.

16 Claims, 3 Drawing Sheets

(51) Int. Cl.
*H01L 27/146* (2006.01)
*A61B 6/03* (2006.01)

(56) References Cited

U.S. PATENT DOCUMENTS

| | | | |
|---|---|---|---|
| 5,677,538 | A | 10/1997 | Moustakas et al. |
| 5,742,659 | A * | 4/1998 | Atac et al. ................... 378/98.8 |
| 7,486,764 | B2 * | 2/2009 | Tkaczyk ................ G01T 1/249 250/370.09 |
| 7,796,174 | B1 * | 9/2010 | Harwit et al. ................. 348/311 |
| 8,445,854 | B2 * | 5/2013 | Hackenschmied ....... G01T 1/00 250/370.09 |
| 2002/0195568 | A1 | 12/2002 | Mori et al. |
| 2003/0052701 | A1 * | 3/2003 | Brown et al. .................. 324/752 |
| 2003/0107001 | A1 | 6/2003 | Baumgartner et al. |
| 2003/0202630 | A1 | 10/2003 | Chen |
| 2004/0113084 | A1 * | 6/2004 | Nakata ..................... G01T 1/26 250/370.01 |
| 2006/0018431 | A1 | 1/2006 | Kanemitsu |
| 2008/0240360 | A1 * | 10/2008 | Jabri .................... A61B 6/5294 378/163 |
| 2009/0014659 | A1 | 1/2009 | Hennessy et al. |
| 2010/0069749 | A1 | 3/2010 | Lu et al. |
| 2013/0009262 | A1 | 1/2013 | Dowben et al. |
| 2013/0161773 | A1 * | 6/2013 | Dierre .............. H01L 27/14601 257/428 |
| 2014/0093038 | A1 * | 4/2014 | Thalhammer ............ G01T 1/24 378/55 |
| 2014/0112432 | A1 * | 4/2014 | Thalhammer et al. .......... 378/19 |
| 2015/0041662 | A1 * | 2/2015 | Thalhammer et al. ..... 250/370.1 |

FOREIGN PATENT DOCUMENTS

| | | |
|---|---|---|
| DE | 102009018877 A1 | 7/2010 |
| DE | 102009019009 A1 | 11/2010 |
| EP | 1744368 A2 | 1/2007 |
| WO | 2010064048 A1 | 6/2010 |

OTHER PUBLICATIONS

Hofstetter et al., "Real-time x-ray response of biocompatible solution gate AlGaN/GaN high electron mobility transistor devices", Applied Physics Letters, vol. 96, pp. 092110-1-3 (2010).

Malinowski et al., "Backside-Illuminated GaN-on-Si Schottky Photodiodes for UV Radiation Detection", IEEE Electron Device Letters, vol. 30, No. 12, pp. 1308-1310 (2009).

Ngu et al., "Array of Two UV-Wavelength Detector Types", IEEE Transactions on Electron Devices, vol. 57, No. 6, pp. 1224-1229 (2010).

Zhang et al., "Backilluminated ultraviolet photodetector based on GaN/AiGaN multiple quantum wells", Applied Physics Letters, vol. 81, No. 24, pp. 4628-4630 (2002).

International Search Report for PCT/EP2012/000946 dated Jun. 29, 2012.

Final Rejection dated Nov. 6, 2015 for U.S. Appl. No. 14/003,082.

Office Action dated Apr. 2, 2015 for U.S. Appl. No. 14/003,082.

* cited by examiner

X-RAY CAMERA FOR THE HIGH-RESOLUTION DETECTION OF X-RAYS

BACKGROUND OF THE INVENTION

The invention relates to a X-ray camera for spatially resolved detection of X-ray radiation. Furthermore, the invention relates to a method for recording an image of an object to be analyzed using X-ray radiation and applications of the X-ray camera.

It is known to use Gallium nitride (GaN) in semiconductor detectors for detection of X-ray radiation. For example, a GaN sensor is described in US 2010/0069749 A1, which emits luminescent light in reaction to a X-ray radiation. The luminescent light is conducted from the sensor via a light guide to a photodetector. This technique has disadvantages, since the combination of the sensor with the light guide represents a sensitive structure and since the detected X-ray radiation is not directly converted in an electric measurement signal. The GaN sensor according to US 2010/0069749 A1 is not suitable due to its structure in particular for an arrangement of a plurality of detectors (array arrangement).

Furthermore, in "Applied Physics Letters" Vol. 92, 2008, pp. 263501, J.-Y. Duboz et al. analyze the suitability of GaN for detection of X-ray radiation. For this purpose, GaN layers, e.g. with a thickness of 110 µm or 480 µm, were deposited on silicon or sapphire substrates and provided with contact electrodes, which formed a Schottky contact with the GaN layer. It was, however, ascertained that a reliable detection was limited to X-ray radiation with an energy value below 20 keV. For practical applications of a radiation detector, for example in dosimetry, a sensitivity to X-ray radiation with an energy value above 20 keV is, however, required.

Finally, M. Hofstetter et al. describe in "Applied Physics Letters" Vol. 96, 2010, pp. 092110, a radiation detector for X-ray radiation, which contains a so-called HEMT ("high electron mobility transistor") with a GaN-based multi-layer system. This radiation detector can likewise have disadvantages due to its multi-layer structure.

In practice, it has shown that the hitherto described GaN-based radiation detectors are not suitable for routine application in dosimetry, in particular due to their complex structure, a complex calibration and/or an insufficient sensitivity. Furthermore, no practical array arrangements of GaN-based radiation detectors, for example in medical engineering, material testing or radiation monitoring were hitherto described.

The objective of the invention is to provide an improved array arrangement of radiation detectors by means of which the disadvantages of conventional techniques are overcome. The array arrangement should be characterized in particular by a simplified structure, a simplified operation and/or an increased sensitivity compared with conventional detectors. The objective of the invention is furthermore to provide a method for X-ray imaging and applications of the array arrangement by means of which disadvantages of conventional techniques for detection of X-ray radiation are overcome.

These objectives are achieved by a X-ray camera and a method having the features of the invention.

DESCRIPTION OF THE INVENTION

According to a first general aspect of the invention, a X-ray camera for detection of X-ray radiation is provided, which comprises a plurality of radiation detectors, which are positioned on a holding device with a predetermined arrangement. The radiation detectors are fixed on the holding device along a predetermined reference line (1D-camera, camera line) or reference surface (2-dimensional camera). The holding device forms a fixture of the radiation detectors. The radiation detectors have a predetermined geometric arrangement on the holding device, so that measurement signals of the radiation detectors can represent a geometric distribution of dosage values in a radiation field of the X-ray radiation and an image of the dosage values can be determined from the measurement signals of the radiation detectors. If the X-ray radiation is modified after an interaction with an object to be analyzed (e.g. radiation transmission or interaction with a surface of the object to be analyzed) in a characteristic manner through properties of the object to be analyzed, the measurement signals of the radiation detectors deliver an image of the object to be analyzed, such as a radiogram or a reflection image.

According to the invention, each radiation detector, i.e. each pixel of the X-ray camera, comprises a carrier substrate, a GaN-based detector layer arranged on the carrier substrate and contact electrodes connected with the detector layer. According to the invention, the detector layer has a thickness, which is less than 50 µm. The carrier substrates of the radiation detectors can be connected with one another to build an integrated substrate. The detector layers can, e.g. through etching, be formed from a uniform GaN-based layer built on the substrate. It is furthermore provided for according to the invention that the contact electrodes form ohmic contacts with the detector layer.

The inventor have found that a single detector layer provided with ohmic contacts with said considerably reduced layer thickness compared with conventional radiation detectors allows a sensitive, reproducible detection of X-ray radiation, which only requires a simple resistance or conductivity measurement. When applying a voltage on the detector layer provided with the contacts, a current measurement provides a resistance or conductivity value. The detector layer acts like a photoconductor the electric resistance of which changes in response to X-ray radiation. A detector current is measurable on the contact electrodes. The detected X-ray radiation is thus directly converted into an electrical measurement signal (detector current, resistance or conductivity value). The conversion yield is in this process great to such an extent that the radiation detector according to the invention can be miniaturized and is particularly well suitable for an array arrangement in the X-ray camera. Preferably, the radiation detector is designed for detection of X-ray radiation in a wide energy range of 1 keV to 300 keV, in particular above 50 keV.

Advantageously, the radiation detectors used according to the invention for constituting the X-ray camera represent beam sensors, which use the photoconductive properties of wide band gap semiconductors. Under the effect of radiation, the conductive detector volume changes. Physically, no predefined electric barrier layer is in this process required as is the case for conventional semiconductor detectors. This allows a novel detection mode for the dosimetry. The detection of the radiation is based upon the principle of a photoconductor with internal amplification properties. No electric barrier layer is required but, rather, a volume-independent measurement by means of the ohmic contacts is provided for. The measurement signal can be represented in different ways (e.g. electronic, graphical, acoustic).

The functional principle of the GaN radiation detectors used according to the invention fundamentally differs from the conventionally available semiconductor detectors for X-ray radiation, for which photo-induced charge carriers are collected by means of an electric field. In contrast, a radiation-induced change in the resistance takes place at the GaN sensors (photoconductor), by changing the detector volume where the charge transfer takes place. Although space-charge zones also occur in the GaN sensors (first and foremost through surface effects), the electric current passes through the semiconductor parallel to these space-charge zones. The irradiation leads to imbalance of free charge carrier concentrations, which change the total volume of the space-charge zones and thus the volume, which contributes to the charge transport. This results in the fact that the amount of the measurement signal is not directly limited to the generation of free charge carriers, but rather a massive internal amplification can take place, whereby increased detection sensitivities compared with conventional techniques are possible.

According to a second general aspect of the invention, a method is provided for recording an image of an object to be analyzed using X-ray radiation, wherein the X-ray camera according to the first aspect of the invention is used. According to the invention, the method comprises a first step of irradiation of the object to be analyzed along at least one predetermined direction of radiation. The object to be analyzed is positioned in the radiation field of a X-ray source. According to the invention, the method furthermore comprises a second step of detection of X-ray radiation after an interaction with the object to be analyzed. In this process, dosage values are recorded in a spatially resolved manner with the radiation detectors of the X-ray camera according to the invention, which values represent the local distribution of the dose in the radiation field of the X-ray radiation. Finally, according to the invention, in a third step, at least one image of the object to be analyzed is reconstructed based on the determined dosage values.

According to a preferred embodiment of the invention, the holding device comprises a holding plate with a fixed, predetermined geometric shape. A holding plate made of a rigid material, such as plastic or ceramic, is preferably provided for. Preferably, the holding device is designed for positioning of the radiation detectors along a straight reference line or a plane reference surface. This advantageously simplifies the reconstruction of an image from the measurement signal of the radiation detectors. For this variant of the invention, the holding plate is preferably formed even. Alternatively, the X-ray camera can be adapted depending on the concrete application to a specific geometric shape of the object to be analyzed. The holding device can be configured in such a manner that the radiation detectors are arranged along a curved reference line or reference surface. For this variant of the invention, the holding device preferably comprises a curved holding plate.

A compact assembly of the X-ray camera can advantageously be achieved if the carrier substrates of the radiation detectors are directly fastened to the holding device, in particular fixed on the holding plate. Particularly preferred is a variant for which the carrier substrates and the holding device form an integral part. The carrier substrates of the radiation detectors are, for this variant of the invention, connected to a common component, in particular to a common holding plate. For example, a wafer, e.g. made of silicon or of sapphire, can simultaneously form the holding plate and the carrier substrates of the radiation detectors.

According to a further preferred embodiment of the invention, the X-ray camera is provided with a housing, which is adapted for accommodating the holding device with the radiation detectors. In the housing, connection lines are preferably accommodated, in addition to the holding device with the radiation detectors, for connecting the contact electrodes of the radiation detectors with a transducer device.

Advantageously, there are different possibilities to provide connection lines for electrical connection of the contact electrodes of the radiation detectors with the transducer device. For example, two connection lines can be provided for each radiation detector, respectively, which connect the contact electrodes with the transducer device. This variant of the invention has a complex structure, since twice as much connection lines and a corresponding interface must be provided for on the transducer device for a specific number of radiation detectors. Advantageously, however, measurement signals (detector currents) can be recorded on all radiation detectors simultaneously. Alternatively, the radiation detectors can be connected groupwise with connection lines in order to detect measurement signals of the radiation detectors serially. For example, a matrix array of radiation detectors can be provided for in straight rows and columns. In this case, each row of radiation detectors can be assigned to a connection line, respectively, and each column of radiation detectors to a connection line, respectively, wherein the measurement signal of an individual radiation detector can be recorded in such a way that a measuring voltage is applied on the connection lines of the associated row and column. Advantageously, the assembly of the X-ray camera is thus simplified, since a considerably reduced number of connection lines is required.

Particularly preferably, the housing is liquid-tight, resistant against acids, resistant against bases, temperature-proof and/or pressure-resistant. This advantageously allows the application of the X-ray camera in extreme environmental conditions, for example for imaging dosimetry in a chemical reactor.

According to a further variant, the X-ray camera can be provided with at least one adhesive surface. Providing the adhesive surface means that the X-ray camera and in particular its housing is formed on at least one surface with an inherent tackiness. The adhesive surface has, for example, an adhesive agent, which allows sticking of the X-ray camera to an object, for example on the surface of an object to be analyzed or of a subject.

A further advantage of the invention is that X-ray radiation is attenuated only negligibly by the material of the holding device and, if applicable of the housing of the X-ray camera. Therefore, the sensitive elements of the radiation detectors, i.e. the detector layers, can be irradiated through the carrier substrate and optionally the holding device and/or the housing. The side of the X-ray camera towards which the carrier substrates of the radiation detectors show is also designated as the front side or radiation entry window of the X-ray camera, whereas the opposite side where the contact electrodes and connection lines of the radiation detectors are located is designated as the rear side of the X-ray camera. Advantageously, the detection of the X-ray radiation through the carrier substrates, i.e. for radiation of the X-ray camera from the front side, is not impaired by the contact electrodes or the connection lines.

According to another preferred embodiment of the invention, the thickness of the detector layers is less than 10 µm, in particular less than 5 µm. Preferably, the thickness of the detector layer is greater than 100 nm, in particular greater than 500 nm. The low thickness of the GaN-based detector layers offers advantages both with respect to the manufacture of the radiation detectors and also with respect to their integration in the X-ray camera. According to further preferred embodiments of the invention, the detector layers of the individual pixels have a surface, which is less than 100 mm$^2$, in particular less than 10 mm$^2$. The surface is preferably greater than 1 µm, in particular greater than 0.1 mm². The radiation detectors used according to the invention can be manufactured by lithographic processes and can therefore be easily miniaturized. The detector size (in particular extension of the sensitive surface) is almost unrestrictedly scalable, in particular in the range of several hundreds µm up to 1 µm, preferred in the size of 30 µm.

Preferably, each radiation detector comprises one single detector layer. In other words, exclusively one layer is provided for, which is fitted with ohmic contacts and is provided for generation of the measurement signal. Particularly preferably, the detector layer consists of GaN, which can optionally contain a doping, for example of iron or carbon.

Further advantages for the miniaturization of the radiation detector result when the contact electrodes consist of two contact electrodes, which are arranged on one side, that is to say in particular on the side of the detector layer opposite the carrier substrate. The contacts are located jointly on the same surface of the detector layer.

According to a further variant, the transducer device can be part of the X-ray camera. The X-ray camera can be equipped with the transducer device, which is, for example, connected with the holding device or optionally enclosed in the housing or connected via a cable with the radiation detector. The transducer device can be adapted for current measurement and voltage supply, data storage and/or data transmission. The current measurement means that the transducer device can be use to detect electrical measurement signals, which are characteristic for the detector currents generated in response to X-ray radiation in the detector layer. If the transducer device according to a particularly preferred variant of the invention is configured for wireless communication with an external control unit and comprises for this purpose in particular an RFID device, this proves advantageous for the application of the X-ray camera in complex structured objects to be analyzed.

The spatial resolution power of the X-ray camera according to the invention is generally determined by the size of the radiation detectors. In order to enhance the resolution power for a given size of the radiation detectors, the X-ray camera can be equipped according to a further advantageous embodiment of the invention with a drive device, by means of which the X-ray camera is movable relative to the object to be analyzed. The drive device is configured for a movement of the arrangement of radiation detectors in one direction that differs from the direction of the X-ray radiation. Preferably, the X-ray camera can be shifted with the drive device vertical to the direction of the X-ray radiation. Through repeated image-taking with a X-ray camera, which is shifted relative to the object to be analyzed, respectively, several images can be recorded, the reconstruction of which result in an image with a spatial resolution, which is better than the size of the radiation detectors.

Preferred applications of the method according to the invention are, for example, in computer-tomography (CT), 2-dimensional X-ray imaging, monitoring of a radiotherapy and/or material or baggage check. For the CT application of the invention, the detection of the X-ray radiation along a number of directions of radiation, which are distributed over at least 180° around the object to be analyzed, is repeated in order to allow reconstruction of a tomographic image of the object. The reconstruction is carried out in this process with reconstruction methods, which are known per se from the prior art.

Furthermore, the radiation detectors used according to the invention have a very large power measurement range, a very large dose rate measurement range and almost no energy-dependency in the diagnostic X-ray range. Due to the extremely wide detection ranges of the GaN sensors (energy and dose rate), the option of biocompatibilization and the option of miniaturization, the GaN sensors offer a considerable potential in the area of medicine as well as in medical-technical applications. Finally, the radiation detector allows a 3-dimensional dosimetry with the option of imaging.

BRIEF DESCRIPTION OF THE DRAWINGS

Further details and advantages of the invention will be explained below with reference to the preferred embodiments of the invention represented in the attached drawings. The figures show as follows:

FIGS. 1A and 1B schematically illustrate a X-ray camera 100 according to the invention in a schematic top view onto the arrangement of the radiation detectors (FIG. 1A) and in a schematic sectional view (FIG. 1B) according to a first embodiment of the invention. The X-ray camera 100 comprises a plurality of radiation detectors 10, which are arranged in the represented exemplary embodiment matrix-shaped in straight rows and columns. All radiation detectors 10 of the X-ray camera 100 have the same structure. Details of the structure of the radiation detectors 10, which each comprise a carrier substrate, a detector layer and contact electrodes, are described below with reference to FIG. 3. In a modified variant of the invention, the radiation detectors can be provided with another geometric distribution, e.g. in circles or as an individual row, and/or with different forms or sizes. In a practical example, the radiation detectors 10 are arranged on a 2-inch wafer, which has a surface of approx. 2000 mm². Cameras with a larger sensitive surface are also possible, e.g. in such a way that several wafers are assembled.

Figure 1:
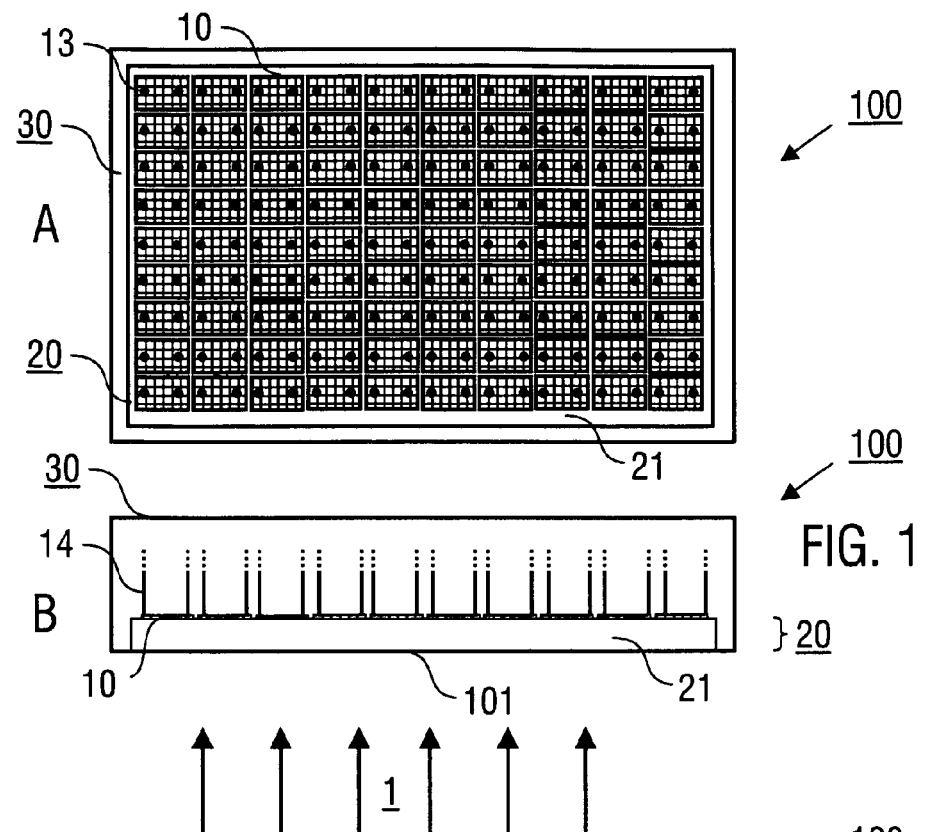
FIGS. 1A and 1B: a schematic top view onto the radiation detectors of a X-ray camera according to the invention and a schematic sectional view of a X-ray camera according to the invention in accordance with a first embodiment of the invention.

The radiation detectors 10 are arranged on a holding device 20, which comprises a holding plate 21. A plane holding plate 21 made of a plastic material, e.g. of polydimethylsiloxane (PDMS), PEN (polyethylenenaphthalate) or polyethylene terephthalate (PET) is provided for. The radiation detectors 10 are sticked to the holding plate 21. The plane holding plate 21 forms a plane reference surface along which the radiation detectors 10 are arranged.

According to a modified variant of the invention, the carrier substrates of the radiation detectors 10 are formed by a common substrate, e.g. made of sapphire, which is simultaneously the holding plate of the holding device 20. In other words, providing the holding plate is not mandatory. For example the sapphire substrate, which the radiation detectors 10 are formed on, is sufficient stable and can therefore serve itself as a holding plate.

Connection lines 14 are provided for on the exposed surface of the radiation detectors 10, which connect the contact electrodes 13 of the radiation detectors 10 with the transducer device (not represented) for recording the measured values and for controlling the X-ray camera 100.

For the represented exemplary embodiment, two connection lines 14 are provided for on each radiation detector 10, which are connected with the electrical circuit. The side of the arrangement the radiation detector 10 facing away from the connection lines 14 forms the front side or the radiation entry window 101 of the X-ray camera 100, whereas the opposite side, where the connection lines 14 are located, forms the rear side of the X-ray camera 100.

For spatially resolved detection of X-ray radiation 1, the X-ray camera 100 is positioned in such a manner that the X-ray radiation 1 is directed towards the radiation entry window 101. The dosage values measured on the individual radiation detectors 10 are recorded in such a way that a measuring voltage is applied to each radiation detector 10 and the detector current flowing on the radiation detector 10 is measured. The detector current depends on the dose of the incident X-ray radiation 1. The detector currents measured provide dosage values from which an image information represented by the X-ray radiation 1 can be reconstructed.

The X-ray camera 100 is provided according to FIG. 1 with a housing 30, which encloses the radiation detectors 10 and the holding device 20 as well as the connection lines 14. On the front side 101 of the X-ray camera 100, the housing 30 be formed by the holding plate 21, i.e. the holding plate 21 can be exposed on the front side 101.

Figure 2:
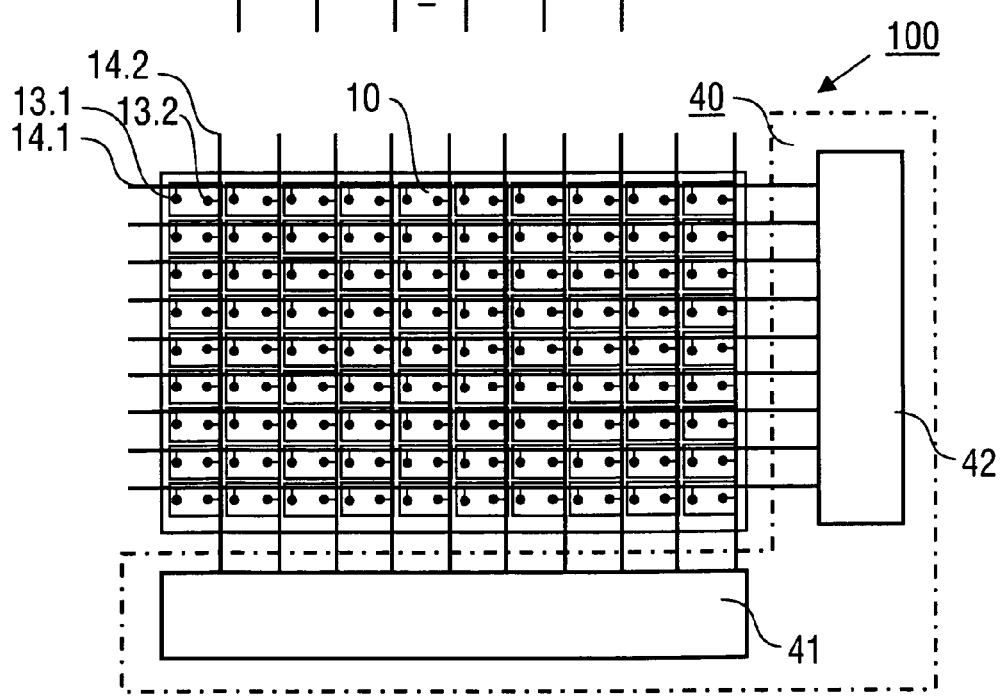
FIG. 2: a schematic top view onto the radiation detectors and connection lines of the X-ray camera according to the invention in accordance with a further embodiment of the invention.

FIG. 2 illustrates schematically a modified embodiment of the invention for which, differing from FIG. 1, not every radiation detector 10 is connected with two connection lines 14, but rather groups of radiation detectors 10 are connected with connection lines 14.1, 14.2. The radiation detectors 10 are arranged matrix-shaped with straight rows and columns. Each radiation detector 10 has a first contact electrode 13.1 and a second contact electrode 13.2. The first contact electrodes 13.1 are connected in rows with a common connection line 14.1, whereas the second contact electrodes 13.2 are connected in columns with a common connection line 14.2. The number of first connection lines 14.1 is thus equal to the number of rows of the matrix arrangement of the radiation detectors 10, while the number of second connection lines 14.2 is equal to the number of columns of the matrix arrangement of the radiation detectors 10. The first and second connection lines 14.1, 14.2 are connected with multiplex circuits 41, 42 of the transducer device 40. The multiplex circuits 41, 42 are configured to sequentially apply measuring voltages to the radiation detectors 10 in order to detect detector currents on the individual radiation detectors 10 for spatially resolved dose measurement.

The radiation detectors 10 of the X-ray camera 100 according to the invention are e.g. structured as is explained in the following with reference to FIGS. 3A and 3B.

Figure 3:
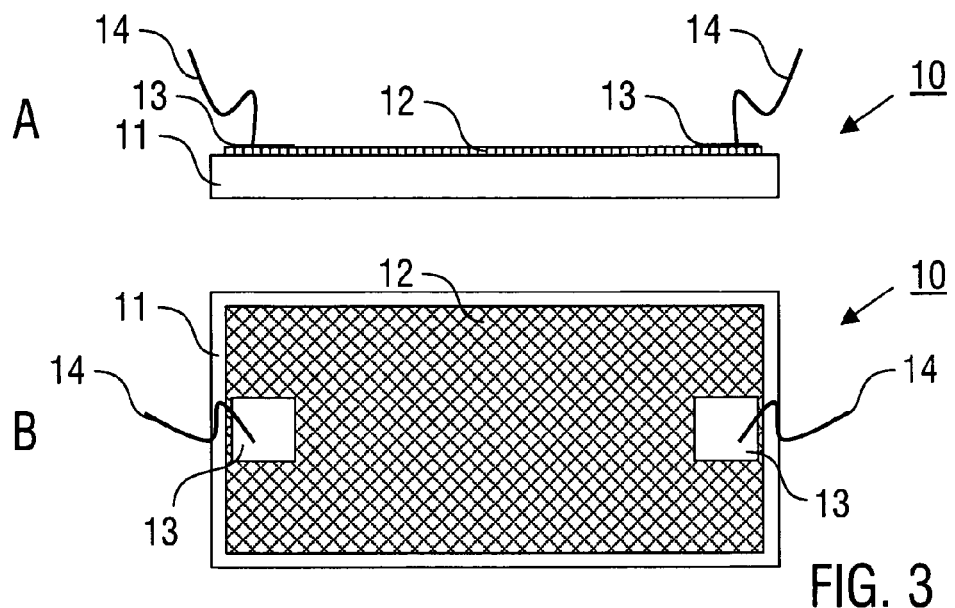
FIGS. 3A and 3B: a schematic sectional view and a schematic top view onto a preferred embodiment of a radiation detector of a X-ray camera according to the invention.

According to FIGS. 3A and 3B, each radiation detector 10 comprises a carrier substrate 11, a detector layer 12 and contact electrodes 13, which can be connected by means of the connection lines 14 with the transducer device for current measurement (not represented). The carrier substrate 11 comprises, for example, sapphire with a thickness of 0.33 mm. The detector layer 12 consists of GaN with a thickness of, for example, 2.5 μm. The contact electrodes 13 consist, for example, of Ti/Al. They are fixed by means of thermal vapour deposition or electron beam vapour deposition on the GaN detector layer 12, so that an ohmic contact is formed between the contact electrodes 13 and the detector layer 12, respectively. The dimensions of the detector layer 12 (FIG. 1B) are for example 0.5 mm·2 mm, whereas the dimensions of the contact electrodes 13 are, for example, 300 μm·300 μm, respectively. The radiation detector 10 is sensitive to X-ray radiation with an energy of 20 keV to 300 keV up to values in the μGy range. As mentioned above, not every detector must have a separate carrier substrate. According to the invention, it is possible to form the individual detector layers (pixels) from a single, coherent detector layer (wafer), for example through etching, on a common substrate. In this process, the substrate is not separated between the pixels.

Figure 4:
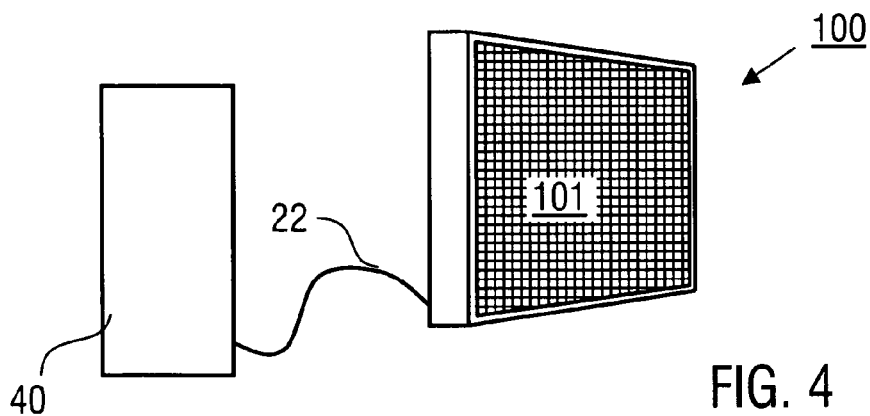
FIGS. 4 and 5: schematic perspective views of different variants of X-ray cameras according to the invention.
Figure 5:
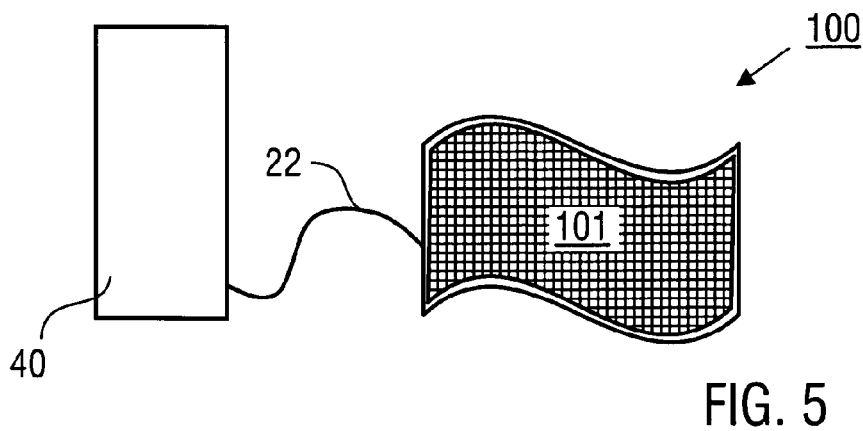

FIGS. 4 and 5 illustrate schematically two variants of the X-ray camera 100 according to the invention with a plane (FIG. 4) or a curved (FIG. 5) shape of the radiation entry window 101. According to FIG. 4, the radiation detectors are accommodated in the housing 20 from which a connection line 22 runs to the transducer device 40, where the recording and storage of the measured values and, if applicable, the reconstruction of the recorded image take place. According to FIG. 5, no housing is provided for. In this case, the radiation detectors 10 are encapsulated with the connection lines on the rear side of the X-ray camera 100 with a plastic layer. In turn, a connection cable 22 leads to the transducer device 40, where the recording and storage of the measured values as well as, optionally, the image reconstruction is provided for.

Figure 6:
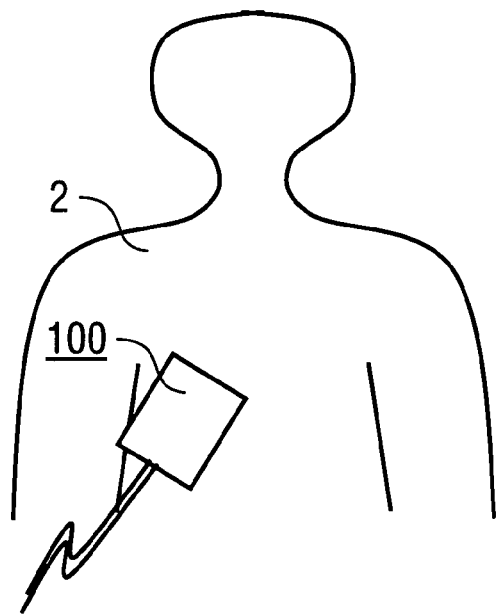
FIG. 6: a schematic illustration of the positioning of a X-ray camera according to the invention on the body of a subject.

FIG. 6 illustrates schematically the positioning of the X-ray camera 100 according to the invention on the skin surface of a subject 2. If the housing of the X-ray camera 100 has an adhesive surface, the X-ray camera 100 can be fixed without further auxiliary agents directly on the skin surface. Alternatively, a subcutaneous arrangement or an arrangement in a cavity of the subject body is possible.

Figure 7:
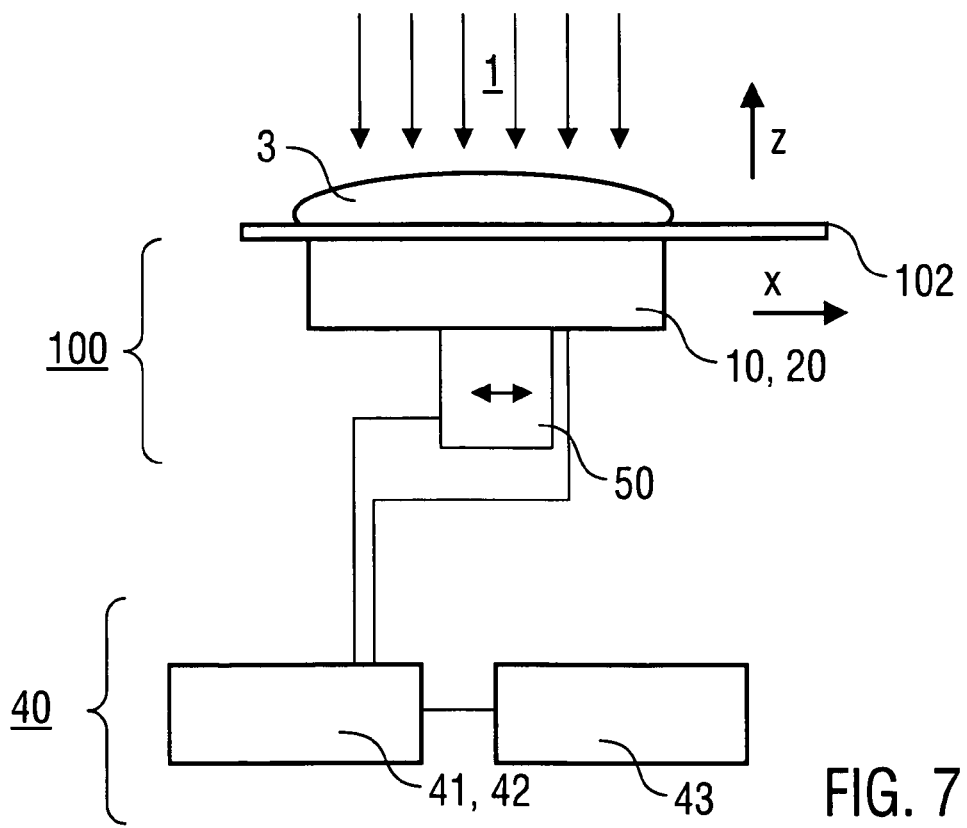
FIG. 7: a schematic illustration of a X-ray camera according to the invention in accordance with a further embodiment of the invention.

FIG. 7 illustrates schematically a further embodiment of a X-ray camera 100 according to the invention, which is adapted, for example, for imaging dosimetry for material testing. The X-ray camera 100 is connected with a drive device 50 by means of which the X-ray camera 100 can be shifted relative to a table 102. The table 102 is provided to receive the object 3 to be analyzed. During radiation of the object 3 to be analyzed with X-ray radiation 1, the radiation field is recorded in a spatially resolved manner with the X-ray camera 100. The drive device 50 and the radiation detectors 10 of the X-ray camera 100 are connected with the transducer device 40, which is provided for recording and storage of the measured values and also for controlling the components 10, 50. The image reconstruction can take place in a separate reconstruction circuit 43, which is connected with the transducer device 40.

To improve the local resolution of the image taken, the drive device 50 can be used to shift the X-ray camera 100 in an offset direction (x direction) vertical to the direction of radiation (z direction) in order to sequentially record several images of the irradiated object 3 to be analyzed. For each image, the X-ray camera is shifted in the offset direction relative to the object to be analyzed. The amount of displacement is less than the expansion Δx of the radiation detectors in the offset direction. If the amount of displacement in the offset direction is an integer part of the expansion Δx/N of the radiation detectors, N images are preferably correspondingly provided for, respectively, with different positions of the X-ray camera relative to the object 3 to be analyzed. From the N images taken, an image can be reconstructed with a local resolution that is improved when compared with a single image.

The features of the invention disclosed in the preceding description, the drawings and the claims can both individually and in combination be of significance for the realization of the invention in its different embodiments.

The invention claimed is:

1. An X-ray camera for spatially resolved detection of X-ray radiation, comprising:
    a plurality of radiation detectors, each of which having a carrier substrate, a detector layer and contact electrodes, wherein the detector layer contains GaN, is arranged on the carrier substrate and has a thickness of less than 50 µm and the contact electrodes form ohmic contacts with the detector layer, and
    a holding device, on which the radiation detectors are arranged along a predetermined reference line or reference surface, wherein
    each of the radiation detectors is provided with a first contact electrode and a second contact electrode, and
    the radiation detectors are arranged in such a way that the carrier substrates are uniformly directed towards a common front side of the X-ray camera, which forms a radiation entry window of the X-ray camera, and the first and second contact electrodes of each of the radiation detectors are uniformly directed towards a common rear side of the X-ray camera, said rear side being opposite to the front side.

2. The X-ray camera according to claim 1, comprising at least one of the features
    the holding device comprises a holding plate with a predetermined geometric form,
    carrier substrates of the radiation detectors are connected with the holding device,
    carrier substrates of the radiation detectors are formed by a common substrate,
    carrier substrates of the radiation detectors form the holding device, and
    carrier substrates of the radiation detectors and the holding device form an integral part.

3. The X-ray camera according to claim 1, wherein the reference line or reference surface is straight, plane or curved.

4. The X-ray camera according to claim 1, wherein a housing is provided for accommodating the holding device with the radiation detectors.

5. The X-ray camera according to claim 4, comprising at least one of the features
    the housing is at least one of liquid-tight, resistant against acids, resistant against bases, temperature-proof and pressure-resistant, and
    the housing is provided with an adhesive surface.

6. The X-ray camera according to claim 1, wherein
    the radiation detectors are arranged matrix-shaped in straight rows and columns.

7. The X-ray camera according to claim 1, comprising at least one of the features
    the thickness of the detector layers is less than 10 µm,
    the detector layers have a surface, which is less than 100 $mm^2$,
    the contact electrodes comprise two contact electrodes, which are arranged on one side on the detector layer, and
    the GaN is doped with Fe or C.

8. The X-ray camera according to claim 7, comprising at least one of the features
    the thickness of the detector layers is less than 5 µm, and
    the detector layers have a surface, which is less than 10 $mm^2$.

9. The X-ray camera according to claim 1, which has a transducer device, which is adapted for at least one of current measurement, data storage and data transmission.

10. The X-ray camera according to claim 9, wherein the transducer device includes an RFID device.

11. The X-ray camera according to claim 1, which has a drive device, which is configured for movement of the radiation detectors relative to an object to be analyzed.

12. A method for accommodating an image of an object to be analyzed using X-ray radiation, with the steps of:
    irradiation of the object to be analyzed along at least one predetermined direction of radiation,
    detection of the X-ray radiation after an interaction with the object to be analyzed, wherein a X-ray camera according to claim 1 is used and dosage values are recorded in a spatially resolved manner with the radiation detectors of the X-ray camera, and
    reconstruction of at least one image of the object to be analyzed from the recorded dosage values.

13. The method according to claim 12, wherein
    the radiation of the object to be analyzed and the detection of the X-ray radiation is repeated along a plurality of different directions of radiation, and
    during the reconstruction, a tomographic image of the object to be analyzed is determined.

14. The method according to claim 12, wherein
    the detection of the X-ray radiation along the at least one predetermined direction of radiation is repeated several times, wherein the X-ray camera is shifted in respectively one offset direction, which deviates from the direction of radiation and wherein the size of the displacement in the offset direction is equal to a fraction of the extension of the radiation detectors in the offset direction.

15. A method of using an X-ray camera according to claim 1, said method comprising mapping dosimetry of X-ray radiation, 2-dimensional X-ray imaging, monitoring of a radiotherapy, material check or baggage check.

16. The method according to claim 15, wherein computer tomography is conducted.

* * * * *